United States Patent [19]

Kuck et al.

[11] Patent Number: 4,905,266
[45] Date of Patent: Feb. 27, 1990

[54] FILM CARTRIDGE SUPPORT FOR BED-LIKE STRETCHER

[75] Inventors: Jay L. Kuck, St. Mary's; Rudolph F. Quinter, Troy, both of Ohio

[73] Assignee: Midmark Corporation, Versailles, Ohio

[21] Appl. No.: 149,749

[22] Filed: Jan. 29, 1988

[51] Int. Cl.[4] .............................................. G03B 42/02
[52] U.S. Cl. .................................. 378/177; 378/179; 378/209; 5/503
[58] Field of Search ...................... 378/167, 177–181, 378/208, 209; 5/60, 66, 503, 506

[56] References Cited

U.S. PATENT DOCUMENTS

| | | | |
|---|---|---|---|
| 2,989,634 | 6/1961 | Ould et al. | 378/177 |
| 3,411,766 | 11/1968 | Lanigan | 378/177 |
| 3,631,242 | 12/1971 | Williams | 378/209 |
| 3,694,653 | 9/1972 | Allard et al. | 378/178 |
| 3,705,984 | 12/1972 | Westenberger | 378/178 |
| 3,968,374 | 7/1976 | Schroeder | 378/181 |
| 4,193,148 | 3/1980 | Rush | 378/177 |
| 4,589,124 | 5/1986 | Ruiz | 378/178 |
| 4,651,364 | 3/1987 | Hayton et al. | 378/177 |
| 4,691,393 | 9/1987 | Kuck | 5/62 |

FOREIGN PATENT DOCUMENTS 1200814  8/1970  United Kingdom ................ 378/177

Primary Examiner—Craig E. Church
Assistant Examiner—John C. Freeman
Attorney, Agent, or Firm—Biebel, French & Nauman

[57] ABSTRACT

The present invention provide an x-ray film cartridge support for a bed-like stretcher. When the x-ray film cartridge support is attached to the crossbars of a stretcher, the support remains stationary thereon during the taking of x-rays especially when the support is attached to the stretcher head end when it is in an inclined position relative to the horizontal foot end. The support is removably mounted so that x-rays of necessary portions of the patient can be taken without movement of the patient on the stretcher.

15 Claims, 3 Drawing Sheets

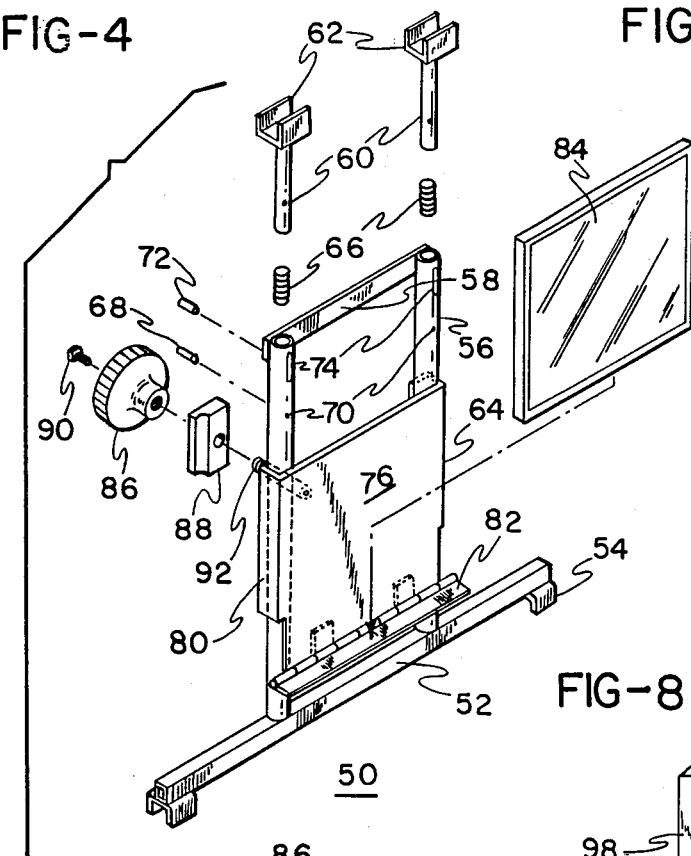
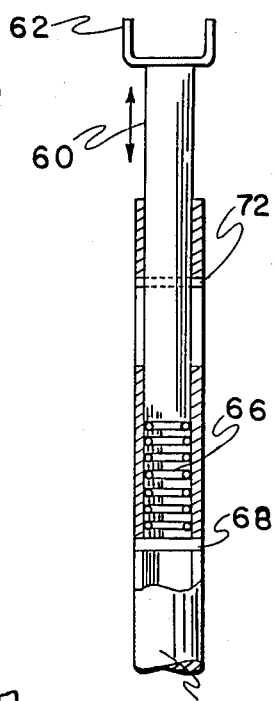
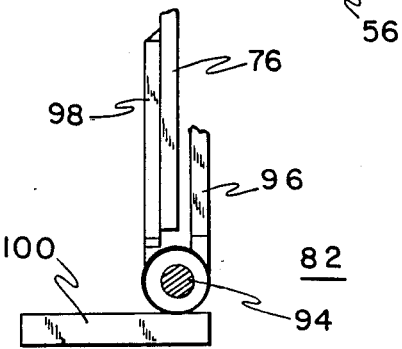
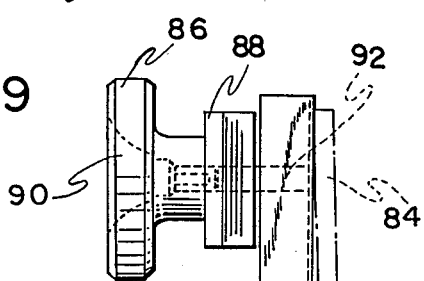
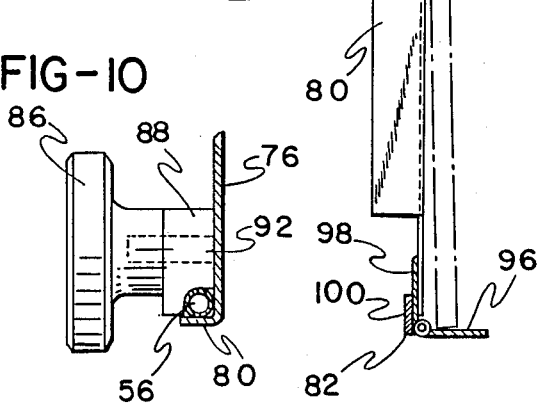
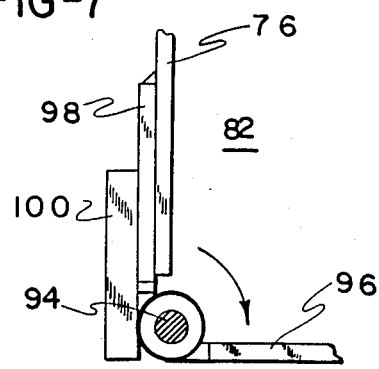

4,905,266

FILM CARTRIDGE SUPPORT FOR BED-LIKE STRETCHER

BACKGROUND OF THE INVENTION

The present invention relates to a film cartridge support, and more particularly, to an x-ray film cartridge support for a bed-like stretcher used in the health care industry.

Various types of bed-like equipment are commonly used in hospitals and other health care facilities. One type of such equipment is referred to as a stretcher which is normally provided with wheels for ease of movement and used in a variety of situations. Such a stretcher is disclosed in commonly assigned U.S. Pat. No. 4,691,393. The wheeled stretcher may be used in emergency room settings and in general hospital service for transporting patients from one location to another. Such a stretcher is of relatively heavy-duty construction and includes a base supported by a plurality of wheels. The base supports the stretcher frame to which a bed portion is attached. The stretcher is also normally provided with side rails which may be selectively raised or lowered. The rails securely hold the patient on the stretcher, but can also be moved out of the way to enable the patient to move or be moved from or onto the stretcher.

Particularly when used in the emergency room, the wheeled stretcher fulfills a variety of roles. For example, the stretcher may serve as a bed during a period of time when a patient is awaiting treatment. The stretcher can also be used to transport the patient. Frequently, the stretcher also serves as an examination table or even as a surgical table for treatment of the patient.

If properly equipped, the wheeled stretcher may serve as an x-ray table for taking x-rays of patients before, during, or after surgical operations. Typical stretchers which can serve as x-ray tables have an x-ray film cartridge support which is located beneath an x-ray transparent horizontal bed surface. Stretchers having x-ray film cartridge supports which are slidably movable beneath horizontal bed surfaces are taught in U.S. Pat. Nos. 2,989,634; 4,193,148; and 4,651,364.

At times in medical practice, a patient requires x-rays of his upper body while he is sitting partially or completely upright. In these situations, in order to allow the patent to sit upright, the head end of the stretcher is raised to an inclined position relative to the foot end of the stretcher which is in a flat horizontal position. The problem which exists in the art is that when the head end of the stretcher is in such an inclined position, the slidably movable x-ray film cartridge supports of the aforementioned patents are useless at the head end of the stretcher because they will not remain in position during the taking of x-rays.

Thus, the need exists in the art for an x-ray film cartridge support which is easily installed at the head end of a stretcher and which remains stationary during the taking of x-rays when the head end is in an inclined position relative to the horizontal foot end of the stretcher. Also, the design of the x-ray film cartridge support must be such so as to enable an operator to x-ray the rquired portions of the patient. The x-ray film cartridge support must also be lightweight so that any operator can readily handle it.

SUMMARY OF THE INVENTION

The present invention provides an x-ray film cartridge support for a bed-like stretcher wherein the stretcher has a frame with crossbars. The cartridge support includes an elongated base, with means for engaging one stretcher crossbar wherein the means are located on each end of the elongated base. Two elongated spaced apart members are connected at their first ends to the elongated base. Means for engaging a second crossbar on the stretcher are provided wherein the means are located on each of the second ends of the two elongated spaced apart members. Means for holding an x-ray film cartridge on the two elongated spaced apart members are provided. The second engaging means comprises rods inserted into each of the second ends of the two elongated spaced apart members wherein each of the rods has a shoe at its first end thereof.

The second end of each of the rods rests on a spring located within each of the two elongated spaced apart members. Each of the springs is supported by a first roll pin which is inserted through each of the two elongated spaced apart members at the tube diameter so that the length of each of the first roll pins is substantially perpendicular to the length of its respective elongated spaced apart member.

Each of the rods is connected to its respective elongated spaced apart member by a second roll pin which is inserted through each of the two elongated spaced apart members at the diameter thereof and each of the rods so that the length of each of the second roll pins is substantially perpendicular to the length of its respective elongated spaced apart member. Each of the two elongated spaced apart members has a slot therein wherein the length of each of the slots is substantially parallel to the length of its respective elongated spaced apart member; upon the application of force to the shoe end of each of the rods, each of the second roll pins moves freely along the length of the slot.

To install the x-ray film cartridge support of the present invention, an operator places the engaging means of the elongated base on a first stretcher crossbar and compresses the spring-loaded rods downwardly. Upon release of the rods, the shoes of the rod ends engage a second stretcher crossbar so that the x-ray film cartridge support is firmly mounted beneath the stretcher. Because the rods are spring-loaded, the x-ray film cartridge support remains stationary during the taking of x-rays especially when the head end of the stretcher is in an inclined position relative to the horizontal foot end of the stretcher.

Because the x-ray film cartridge support is typically mounted on crossbars which run across the width of a stretcher, the x-ray film cartridge support of the present invention can be installed at any location across the width of the stretcher. An operator simply installs the cartridge support at the stretcher width position which corresponds to the patient area which needs to be x-rayed. A patient never has to move parallel to the stretcher width in order to be x-rayed because the cartridge support can be moved systematically across the entire stretcher width in order to x-ray entire width of a patient if necessary.

The means for holding an x-ray film cartridge comprises an x-ray film holder having a plate with two ends which contact the two elongated spaced apart members and a third end comprising a hinge for holding an x-ray film cassette. A clamping knob and clamp are fastened to the plate near one of the two elongated spaced apart members and a portion of the clamp contacts the elongated spaced apart member.

To reposition the x-ray film holder on the two elongated spaced apart members, the clamping knob is loosened, the x-ray film holder is moved to a new position on the members, and the clamping knob is tightened so that the x-ray film holder is stationary on the members. The x-ray film holder can be moved on the members before or after the x-ray film cartridge support is installed on the stretcher crossbars.

Because the x-ray film holder can be moved along the length of the member, a patient need not be moved parallel relative to the stretcher head end length in order to be x-rayed because after the x-ray film cartridge support is installed at the proper stretcher width position, the film holder can be moved systematically down the length of the two elongated spaced apart members to x-ray the entire upper body length of a patient if necessary. A situation wherein such movement may be required is when a patient has a spinal injury; in this case, the patient's entire spine may have to be x-rayed. Because the x-ray film holder is movable along the entire length of the members and th x-ray film cartridge support is movable across the entire width of the stretcher, the entire cross section of the stretcher head end can be covered so that the patient need not move on the x-ray stretcher. The x-ray film cartridge support of the present invention is also lightweight so that any operator can eadily handle it.

The hinge of the x-ray film holder comprises a pin having two leaves and a hinge stop connected thereto. The first leaf is attached to the holder plate. In a first position, the second leaf supports an x-ray film cassette. The second leaf and hinge stop can rotate by 90° to a second position so that the second leaf will lay flat, i. e., be parallel to the x-ray film holder plate. As such, the x-ray film cartridge support of the present invention can be used in combination with known slidably movable x-ray film cartridge supports wherein when a stretcher is in a horizontal position and the second leaf is flat, a known slidably movable x-ray film cartridge support can slide over the x-ray film cartridge support of the present invention without interference.

As such, the x-ray film cartridge support of the present invention fulfills the need in the art.

The present invention also provides a bed-like stretcher for supporting a patient comprising a frame for supporting a bed surface having a length and a width and defining a head end and a foot end, and a base. Fixing means fix the head end in any selected pivotal position within an available range relative to the foot end. A releae rod is connected to the fixing means for selectively releasing the fixing means thereby permitting pivotal movement of the head end. The aforementioned xray cartridge support is removably mounted to the frame at the head end.

Accordingly, it is an object of the present invention to provide an x-ray film cartridge support for a bed-like stretcher; to provide such a support which is easily installed on the stretcher; to provide such a support which remains stationary during the taking of x-rays when the head end is in an inclined position relative to the horizontal foot end of the stretcher; to provide such a support which is movable around the entire cross section of the stretcher head end so that the patient need not move on the x-ray stretcher; to provide such a support which is lightweight; and to provide such a support which will not interfere with the movement of a known slidably movable x-ray film cartridge support.

Other objects and advantages of the present invention will be apparent from the following description, the accompanying drawings, and the appended claims.

BRIEF DESCRIPTION OF THE DRAWINGS

FIG. 4 is a three-quarter view of the x-ray film cartridge support, shown partially exploded;

FIG. 6 is a view of a rod of FIG. 4 inserted in an elongated member;

FIG. 7 is a side view of the hinge of FIG. 4 wherein the hinge is in a shelf-like position for holding an x-ray film cassette;

FIG. 8 is a side view of the hinge of FIG. 7 wherein the leaf and hinge stop have been rotated by 90°;

FIG. 9 is a side view of the clamping mechanism of FIG. 4; and

FIG. 10 is a top view of the clamping mechanism of FIG. 4.

DETAILED DESCRIPTION OF THE PREFERRED EMBODIMENTS

The present invention is generally applicable to a wheeled, bed-like stretcher typically found in hospital emergency rooms and other hospital environments. The present invention provides an x-ray film cartridge support to be mounted to the bed-like stretcher. It will be recognized, however, that the present invention is also usable with other bed-like devices, including fixed examination tables, hospital beds, and the like.

Figure 1:
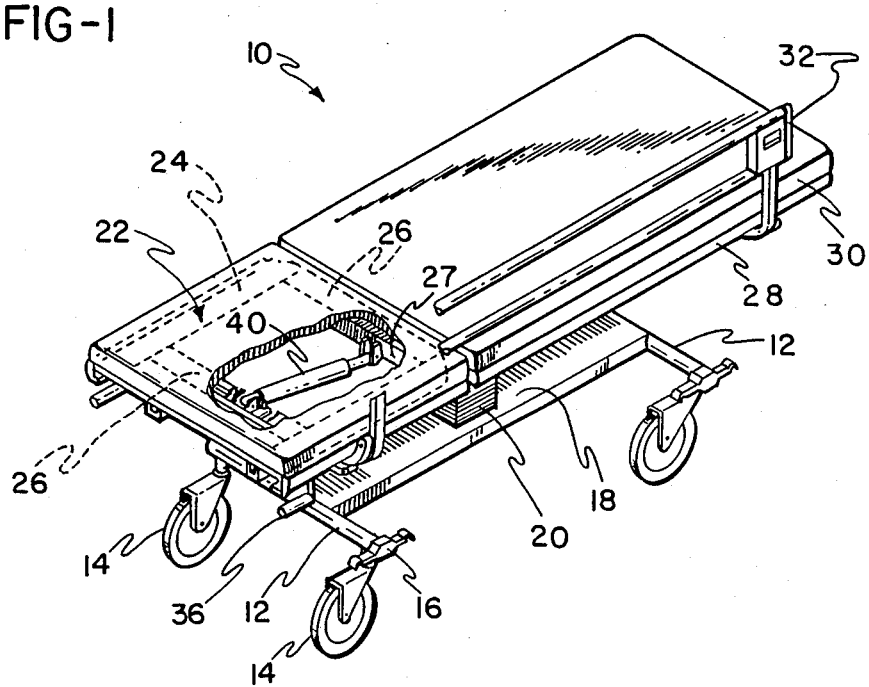
FIG. 1 is a three-quarter view of a bed-like stretcher with which the present invention may be used, wherein several of the stretcher components are shown broken away for clarity.

Referring generally to FIG. 1, a stretcher 10 is shown as having a wheeled base including supportive cross members 12. A wheel assembly 14 is provided at each end of the members 12, and a brake mechanism 16, the structure of which is well known in the art, is provided for locking the wheels to prevent movement of stretcher 10 when desired. Cross members 12 are connected by a base plate 18, which in turn supports a hollow vertical column 20.

Column 20 is connected by an axle (not shown) to a stretcher frame 22. Stretcher frame 22 includes peripheral frame members 24 wherein one frame member 24 extends along each side of frame 22. Frame members 24 are preferably formed as aluminum extrusions and include rubber protective strips (not shown) attached thereto. Stretcher frame 22 also includes cross members 26 and 27. Frame members 24 also support bed surface 28 upon which an appropriate mattress 30 is placed. Bed surface 28 and mattress 30 are selected to be x-ray transparent.

To prevent a patient occupying stretcher 10 from accidentally falling from the stretcher, a side rail assembly 32 is provided along each side of the stretcher. Only a single side rail is shown in FIG. 1 for purposes of clarity, with the rail shown having the central portion broken away. However, it will be understood that identical and complete side rail assemblies 32 are mounted in identical fashion to each side of the stretcher.

Figure 2:
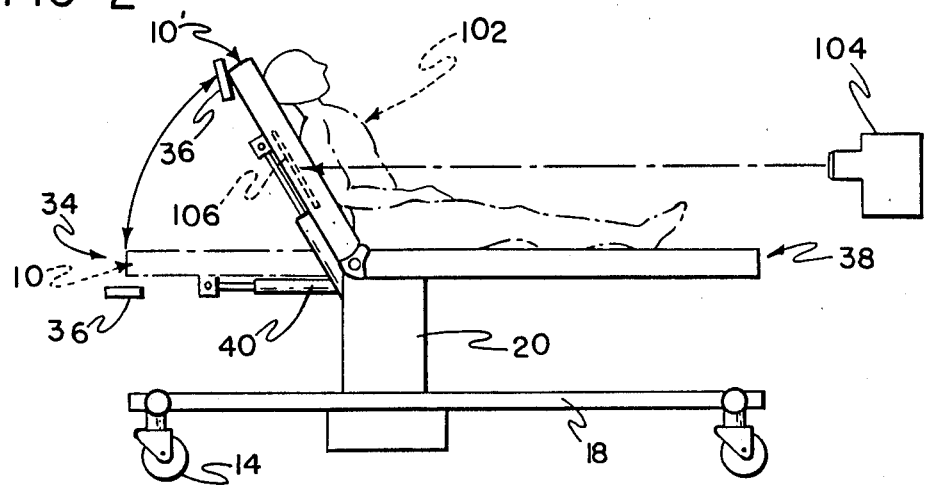
FIG. 2 is a side schematic view of the stretcher wherein the head end is in an inclined position relative to the foot end.

Referring now to FIG. 2, the inclined movement of the head end 34 of the stretcher bed 10 can be seen. Handles 36 are mounted at each side of the stretcher 10 near the head end 34 of stretcher 10 for releasing the head end 34 for pivotal movement.

Frequently, stretcher 10 is located in a flat horizontal position as shown in dotted lines in FIG. 2. Depending upon the treatment required for a patient, the stretcher 10 can be moved to the position as shown in solid lines by stretcher 10' wherein the head end 34 is inclined relative to the foot end 38. The angle of inclination varies depending upon the treatment required.

Figure 3:
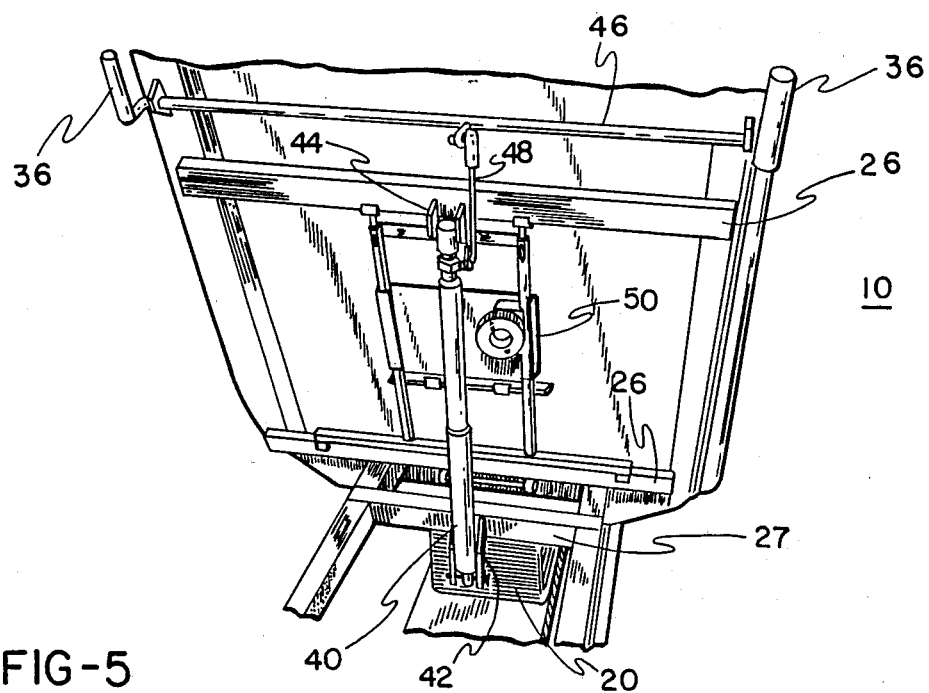
FIG. 3 is an underneath view of the inclined head end of the stretcher having the x-ray film cartridge support of the present invention mounted thereon.

To permit the pivotal movement of the head end 34 relative to the foot end 38, a gas spring 40 is used as shown in FIGS. 1, 2, and 3. Gas spring 40 may be any appropriate commercially available gas spring such as those available from Gas Spring Corporation of Colmar, Pa. Referring to FIG. 3, the gas spring 40 is mounted to crossbar 27 by brackets 42 and to crossbar 26 by brackets 44. Handles 36 are connected to shaft 46 which is connected to actuator rod 48. Pivotal movement of handles 36 causes shaft 46 to rotate which causes actuator rod 48 to actuate gas spring 40 as necessary to raise or lower head end 34.

Within gas spring 40, a piston is provided with a fluid passage extending therethrough and a valve for selectively closing and opening the passage. Fluid is contained on each side of the piston. Downward movement of a release rod opens the valve to permit fluid flow from one side of the piston to the other. The fluid flow counterbalances the weight of the head end 34 of the stretcher frame 22 during angular movement thereof. As such, gas spring 40 allows for pivotal movement of the head end 34 in order to properly position the patient.

Figure 5:
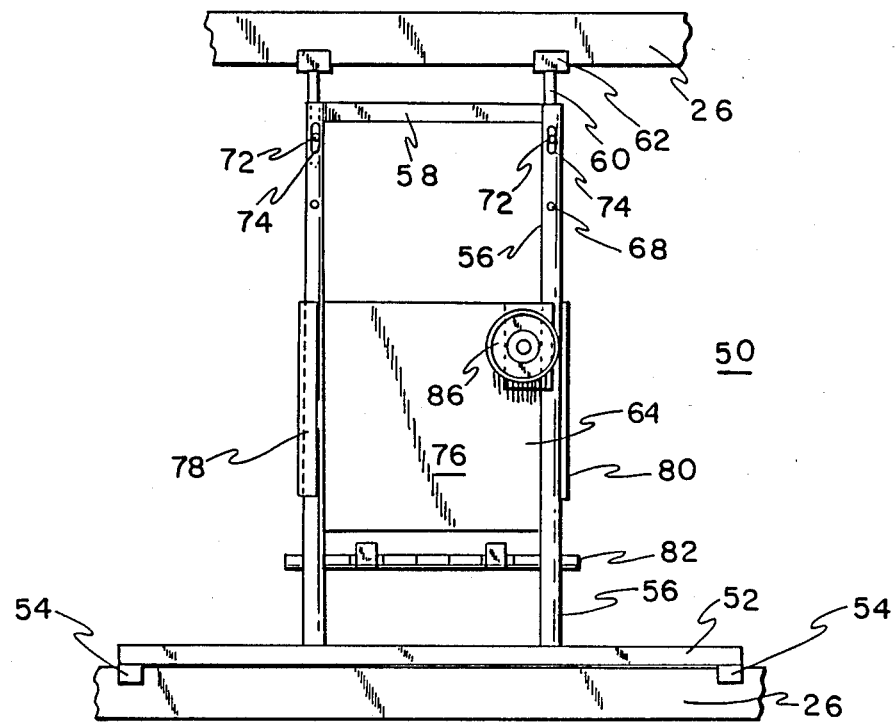
FIG. 5 is a front view of the x-ray film cartridge support.

The x-ray film cartridge support 50 of the present invention is shown partially exploded in a back view in FIG. 4 and a front view in FIG. 5. The x-ray film cartridge support 50 comprises an elongated base 52 having means for engaging crossbars on the stretcher wherein the means are located on each end of the elongated base. Typically, the engaging means comprises a shoe 54 located at each end of the elongated base. Two elongated spaced apart members 56 are connected at their first ends to the elongated base 52. A strap 58 can be connected to the second ends of the two elongated spaced apart members 56 wherein strap 58 is substantially parallel to elongated base 52.

Means for engaging the crossbars of the stretcher are provided wherein the means are located on each of the second ends of the two elongated spaced apart members 56. The engaging means comprise rods 60 inserted into each of the second ends of the members 56 and each of the rods 60 has a shoe 62 at its first end thereof. It is suggested that petroleum jelly be applied to rods 60 before insertion into members 56 because rods 60 must move freely after the assembly is completed. The shoes 62 are designed to engage crossbars on a stretcher. An x-ray film holder 64 is mounted on the two elongated spaced apart members 56. Preferably, elongated base 52, shoes 54, members 56, strap 58, rods 60, shoes 62, and x-ray film holder 64 are all formed from lightweight metals so that any operator can readily handle the x-ray film cartridge support 50 of the present invention.

Referring to FIGS. 4 and 6, the second end of each of the rods 60 rests on a spring 66 located within each of the members 56. Each of the springs 66 is supported by a first roll pin 68 which is inserted diametrically through each of the members 56 at holes 70 so that each of the first roll pins 68 is substantially perpendicular to its respective elongated spaced apart member 56. Each of the rods 60 is connected t its respective member 56 by a second roll pin 72 which is inserted diametrically through each of the rods 60 and through the members 56 at slots 74 so that each of the second roll pins 72 is also substantially perpendicular to its respective member 56. Typically, for ease of assembly, first roll pin 68 is inserted through member 56, spring 66 is dropped into member 56 onto first roll pin 68, rod 60 is dropped into member 56 onto spring 66, and second roll pin 72 is inserted through member 56 and rod 60. Each of the slots 74 is substantially parallel to its respective member 56 so that upon the application of force to the shoe end of each of rods 60, each of the second roll pins 72 moves freely along the length of its respective slot 74.

Referring to FIGS. 4 and 5, the x-ray film holder 64 comprises a plate 76 having two ends 78 and 80 which contact and are slidable along the two elongated spaced apart members 56 and a third end comprising a hinge 82 for holding an x-ray film cassette 84. Typically, nylon tape is applied to the full length of the inner surfaces of ends 78 and 80 for ease of movement along members 56. Preferably, plate 76 and hinge 82 are formed from lightweight metals.

Referring to FIGS. 4, 9, and 10, the x-ray film holder 64 further comprises a clamping knob 86 preferably formed from a phenolic resin and a clamp 88 which is preferably formed of aluminum and has a cut out section designed to contact member 56. A socket head screw 90 with a washer (not shown, is inserted through clamping knob 86 and clamp 88, and screwed into threaded cylinder 92 on plate 76. Clamping knob 86 can be turned so as to loosen the x-ray film holder 64 and move it to a new location along the length of members 56. After moving the x-ray film holder 64, the clamping knob 86 can then be turned in the opposite direction so that the x-ray film holder 64 remains stationary relative to the members 56.

Referring to FIG. 7, hinge 82 comprises a pin 94 having a shelf leaf 96, another leaf 98, and a hinge stop 100 connected thereto. Leaf 98 secures the hinge 82 to plate 76. As shown in FIG. 9, shelf leaf 96 supports the x-ray film cassette 84 thereon during the taking of x-rays. When the x-ray film cassette 84 is removed from shelf leaf 96, leaf 96 and hinge stop 100 can be rotated from the first position of FIGS. 7 and 9 to a second position as shown in FIG. 8. When shelf leaf 96 is in this position wherein it is parallel to plate 76, a known slidably movable x-ray film cartridge support can slide over the x-ray film cassette holder 64 without interference.

To install the x-ray film cartridge support 50 to a stretcher, an operator places the shoes 54 of the tubular member 52 on a first stretcher crossbar 26 and compresses the spring-loaded rods 60 downwardly. Upon release of the rods 60, the shoes 62 of the rods 60 engage a second stretcher crossbar 26 so that the x-ray film cartridge support 50 is firmly mounted beneath the stretcher as shown in FIGS. 3 and 5.

to take x-rays of a patient 102 as shown in FIG. 2, an oprator uses a commercially available x-ray source 104 to direct x-rays onto patient 102 and the x-ray film cartridge support whch is indicated by the dotted block 106. Because the rods 60 are spring-loaded, the x-ray film cartridge support 50 remains stationary during the taking of x-rays especially when the head end 34 is in an inclined position relative to the horizontal foot end 38 of the stretcher. The operator can then move the x-ray film cartridge support 50 to another location on the crossbars 26 as shown in FIG. 3 in order to take x-rays of another patient area. Also, the operator can then move the x-ray film holder 64 to another location on the members 56 in order to take x-rays of another patient area.

Although the x-ray film cartridge support 50 of the present invention is particularly useful beneath an inclined stretcher head end, the x-ray film cartridge support 50 may be useful beneath an inclined stretcher foot end. Also, although the x-ray film cartridge support 50 of the present invention is particularly useful beneath an inclined stretcher end, the x-ray film cartridge support 50 may be useful beneath a horizontal stretcher end. As such, the x-ray film cartridge support 50 could be installed on a stretcher head end whether it is in a horizontal or inclined position.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. An x-ray film cartridge support for a bed-like stretcher, said stretcher having a frame with crossbars, said x-ray film cartridge support comprising:
   an elongated base having a first base end and a second base end;
   first means for engaging one of said crossbars wherein the first means is located on both said first base end and said second base end of said elongated bae;
   an elongated spaced apart member, having a first and a second end, said member connected at said first end to said elongated base;
   second means for engaging another of said crossbars wherein said second means is located on said second end of said elongated spaced apart member, said second engaging means comprising a rod inserted into said second ends of said elongated spaced apart member wherein said rod has a rod first end and a rod second end, said rod first end having a shoe thereat, said rod second end resting on a spring located within said elongated spaced apart member; and
   means for holding an x-ray film cartridge on said two elongated spaced apart member.

2. The x-ray film cartridge support of claim 1 wherein said spring is supported by a first roll pin which is inserted diametrically through said elongated spaced apart member so that said first roll pin is substantially perpendicular to the elongated spaced apart member through which said first role pin is inserted.

3. The x-ray film cartridge support of claim 2 wherein said fod is connected to said elongated spaced apart member by a second roll pin which is inserted diametrically through said elongated spaced apart member and said rod so that said second roll pin is substantially perpendicular to said elongated spaced apart member.

4. The x-ray film cartridge support of claim 3 wherein said elongated spaced apart member has a slot therein wherein the length of said slot is substantially parallel to the length of said respective elongated spaced apart member such that upon the application of force to the rod first end, said second roll pin moves freely along said length of said slot of said elongated spaced apart member.

5. The x-ray film cartridge support of claim 1 wherein said means for holding an x-ray film cartridge comprises a plate having an end which contacts said elongated spaced apart member and a third end comprising a hinge for holding an x-ray film cassette.

6. The x-ray film cartridge support of claim 5 wherein said means for holding an x-ray film cartridge further comprises a clamping knob and a clamp wherein said clamping knob and said clamp are fastened to said plate near said elongated spaced apart member and a portion of said clamp contacts said elongated spaced apart member.

7. The x-ray film cartridge support of claim 6 wherein said hinge comprises a pin having two leaves and a hinge stop connected to said pin.

8. The x-ray film cartridge support of claim 7 wherein said leaves comprise a first leaf and a second leaf, said first leaf attached to said plate, said second leaf and said hinge stop being free to rotate by 90°.

9. A bed-like stretcher for supporting a patient comprising:
   a frame for supporting a bed surface having a length and a width and defining a head end and a foot end, said frame traversed by at least two crossbars;
   a base having a first base end and a second base end;
   fixing means for fixing said head end in any selected pivotal position within an available range relative to said foot end;
   a release rod connected to said fixing means for permitting pivotal movement of said head end; and
   an x-ray film cartridge support removably mounted to said frame at said head end, said x-ray film cartridge support assembly comprising an elongated base, first means for engaging one of said crossbars wherein said first means is located on both said first base end and said second base end of said elongated base, an elongated spaced apart member having a first end which is connected to said elongated base, second means for engaging another of said crossbars wherein said second means is located on end said second end of said elongated spaced apart member, said second engaging means comprising a rod inserted into end of second end of said elongated spaced apart member wherein end of said rod has a rod first end and a rod second end, said rod first end having a shoe thereat, said rod second end resting on a spring located within said elongated spaced apart member and means for holding an x-ray film cartridge on said elongated spaced apart member.

10. The bed-like stretcher of claim 9 wherein said spring is supported by a first roll pin which is inserted through said elongated spaced apart member at the diameter thereof so that the length of said first roll pin is substantially perpendicular to the length of the elongated spaced apart member through which said first roll pin is inserted.

11. The bed-like stretcher of claim 10 wherein said rod is connected to said elongated spaced apart member by a second roll pin which is inserted through said elongated spaced apart member at the diameter thereof and said rod so that the length of said second roll pin is substantially perpendicular to the length of said elongated spaced apart member.

12. The bed-like stretcher of claim 11 wherein said elongated spaced apart member has a slot therein wherein the length of said slot is substantially parallel to the length of said elongated spaced apart member such that upon the application of force to the rod first end, said second roll pin moves freely along said length of said slot of said elongated spaced apart member.

13. The bed-like stretcher of claim 9 wherein said means for holding an x-ray film cartridge comprises a plate having an end which contacts said elongated spaced apart member and a third end comprising a hinge for holding an x-ray film cassette.

14. The bed-like stretcher of claim 13 wherein said means for holding an x-ray film cartridge further comprises a clamping knob and a clamp wherein said clamping knob and said clamp are fastened to said plate near said elongated spaced apart member and a portion of said clamp contacts said elongated spaced apartment member.

15. The bed-like stretcher of claim 14 wherein said hinge comprises a pin having two leaves and a hinge stop connected to said pin.

* * * * *

UNITED STATES PATENT AND TRADEMARK OFFICE
CERTIFICATE OF CORRECTION

PATENT NO. : 4,905,266
DATED : February 27, 1990
INVENTOR(S) : Jay L. Kuck, et al It is certified that error appears in the above-identified patent and that said Letters Patent is hereby corrected as shown below:

Column 7, Claim 3, line 61, "fod" should be --rod--.

Column 8, Claim 9, line 49, "end of" should be --said--;

line 50, "end of" should be deleted.

Signed and Sealed this

Fourteenth Day of July, 1992

*Attest:*

DOUGLAS B. COMER

*Attesting Officer*   *Acting Commissioner of Patents and Trademarks*